(12) United States Patent
Kroll

(10) Patent No.: US 7,292,886 B1
(45) Date of Patent: Nov. 6, 2007

(54) BIFOCAL CARDIAC STIMULATION DEVICE AND METHODS

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 571 days.

(21) Appl. No.: 10/762,160

(22) Filed: Jan. 20, 2004

(51) Int. Cl.
*A61N 1/368* (2006.01)
*A61N 1/39* (2006.01)

(52) U.S. Cl. .............................. 607/5; 607/9; 607/122; 607/15

(58) Field of Classification Search ..................... 607/4, 607/5, 9, 122, 15
See application file for complete search history.

(56) References Cited

U.S. PATENT DOCUMENTS

| | | | |
|---|---|---|---|
| 4,289,144 A | 9/1981 | Gilman | 128/785 |
| 4,712,555 A | 12/1987 | Thornander et al. | 128/419 PG |
| 4,788,980 A | 12/1988 | Mann et al. | 128/419 PG |
| 4,940,052 A | 7/1990 | Mann et al. | 128/419 PG |
| 4,998,975 A * | 3/1991 | Cohen et al. | 607/5 |
| 5,107,834 A * | 4/1992 | Ideker et al. | 607/5 |
| 5,466,254 A | 11/1995 | Helland | 607/123 |
| 5,476,483 A | 12/1995 | Bornzin et al. | 607/17 |
| 5,948,014 A * | 9/1999 | Valikai | 607/123 |
| 5,978,704 A | 11/1999 | Ideker et al. | 607/5 |
| 6,205,357 B1 | 3/2001 | Ideker et al. | 607/14 |
| 6,253,106 B1 | 6/2001 | Legay et al. | 607/9 |
| 2002/0193836 A1 | 12/2002 | Schmidt | 607/130 |
| 2004/0122497 A1* | 6/2004 | Zhang et al. | 607/122 |

FOREIGN PATENT DOCUMENTS

| | | |
|---|---|---|
| EP | 0925806 A1 | 6/1999 |
| WO | WO 02/087501 A2 | 11/2002 |
| WO | WO 02/087501 A3 | 11/2002 |

OTHER PUBLICATIONS

Jasbir S. Sra, "Cardiac Resynchronization in Heart Failure," *Indian Heart J*, 2003; vol. 55, pp. 125-146.

N. Nikoloudakis, et al., "Bifocal Right-Atrial Stimulation for Prevention of Atrial Fibrillation After CABG Surgery," *Thoracic Cardiovasc Surg*, 2001; Thema: Permanent Poster; pp. 56 (Abstract).

A. Le Helloco, et al., "Comparaison de al Stimulation Apicale et Infundibulaire Chez les Patients Atteints d'une Cardiomyopathie Dilatée Preimitive ou Ischémique," *Arch Mal Coeur Vaiss*, 1999(Janvier); vol. 92, No. 1, pp. 19-26.

Roberto Zayas, et al., "Multisite Stimulation in Patients with Severe Ventricular Disfunction," *Rev Cubana Med*, 2003; vol. 42, No. 2, pp. 1-2 (Abstract).

(Continued)

*Primary Examiner*—Kennedy J. Schaetzle

(57) ABSTRACT

A cardiac stimulation system for implantation in a patient is disclosed. The cardiac stimulation system comprises first and second electrodes configured for positioning in a bifocal arrangement. A first lead system is adapted for carrying the first and second electrodes in the right ventricle in accordance with the bifocal arrangement and along the high basal region of the heart proximate the septum. A third electrode is adapted for positioning outside the right ventricle. The system further comprises a power supply and a controller. The controller is coupled to the power supply and operates to activate the first, second and third electrodes to deliver pulse therapy to the heart according to predetermined criteria.

22 Claims, 8 Drawing Sheets

OTHER PUBLICATIONS

Athanasios G. Manolis, "Towards a Physiologic Cardiac Pacing. Evolution in the Modern Era," *Hellenic J. Cardio*, 2000; vol. 41, pp. 516-523.

Jose Carlos Pachon Mateos et al., "Right Ventricular Bifocal Stimulation in the Treatment of Dilated Cardiomyopathy with Heart Failure," *Arq Bras Cardiol*, vol. 73 (No. 6)(1999), pp. 492-498.

* cited by examiner

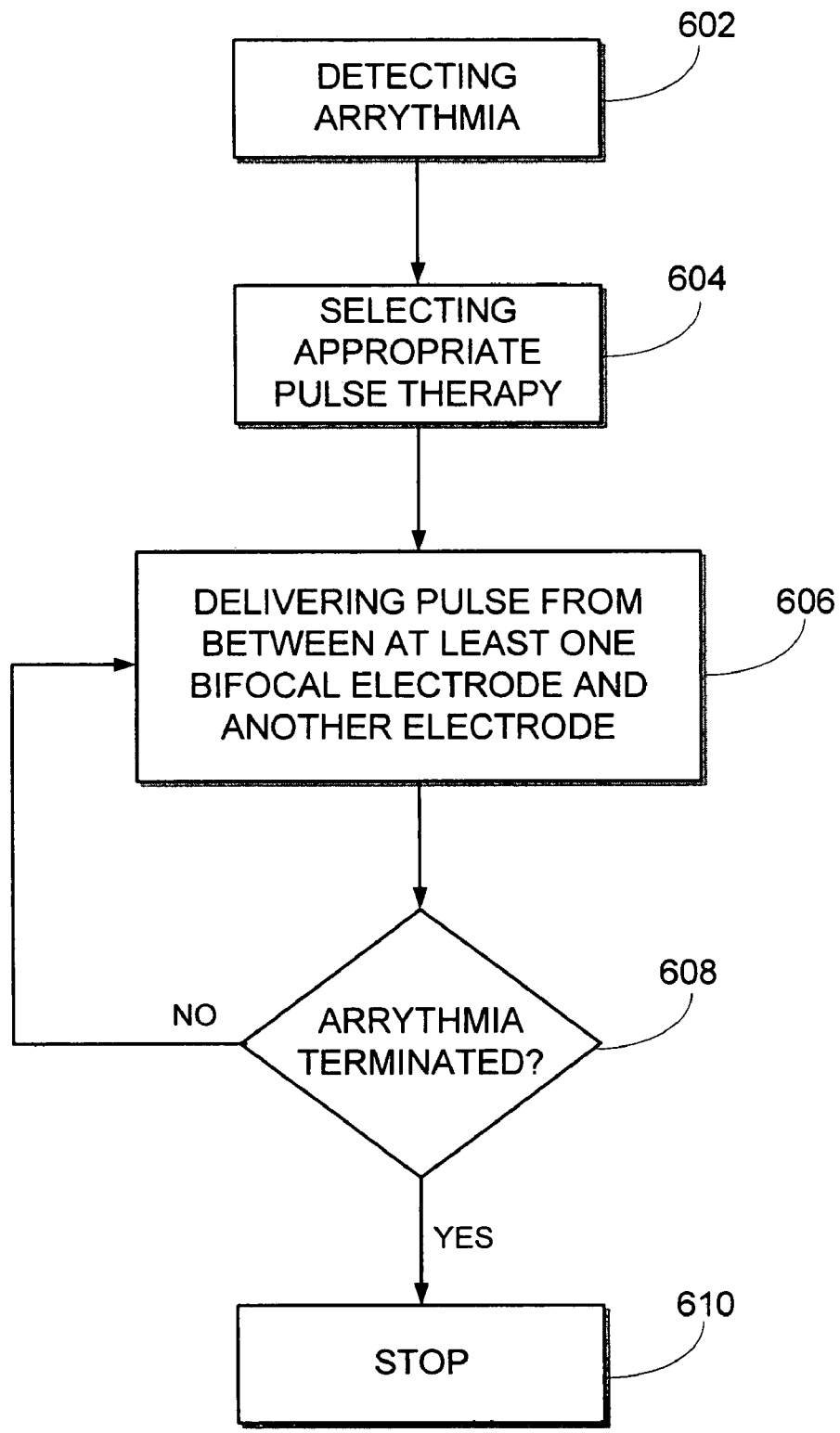

BIFOCAL CARDIAC STIMULATION DEVICE AND METHODS

FIELD

The following relates generally to cardiac stimulation devices, and more particularly to pulse delivery systems and methods for maximizing atrial and ventricular pulse therapy.

BACKGROUND

Cardiac stimulation devices, such as pacemakers, implantable cardioverter defibrillators (ICD's) or congestive heart failure devices (CHF) play an important role in many cardiac patient lives. These devices typically monitor cardiac arrhythmias, and in most cases, provide a form of electrical stimulation therapy to the heart as needed. Modern electronics have enabled the miniaturization of these devices for implantation in a patient for constant monitoring while the patient lives a normal life.

One of the features of a cardiac stimulation device (CSD) is the ability to apply a stimulation pulse across a desired portion of the cardiac tissue, and achieve a specific response in the form of a desired contraction of the heart tissue in that area. The devices typically employ a pulse generator disposed in a metallic housing, and one or more leads coupled to the output of the generator. Each lead carries one or more electrodes for directing the pulse across the desired cardiac tissue. Consequently, the overall construction of the pulse generator output circuitry, the lead configurations, and the electrode configurations are important for maximum flexibility in positioning and configuring the leads and electrodes.

An undesirable side-effect often associated with conventional atrial cardioversion and ventricular defibrillation involves discomfort experienced by the patient during pulse therapy. Much of the discomfort results from current conduction through non-cardiac tissue along shock vectors directed partially outside the heart. While the patient is often unconscious during ventricular defibrillation, often rendering the discomfort issue moot, this is not typically the case for low energy pulse therapies.

FIG. 1 illustrates some available shock vectors associated with conventional atrial cardioversion techniques. Shock vectors are generally defined according to electrode placement. Typically, electrodes 20, 22 and 24 are disposed in the right atrium (RA), right ventricle (RV), and coronary sinus or other cardiac vein. The metallic housing of a cardiac stimulation device 26 often serves as a return electrode. A first current conduction path, or current vector CV1, is defined by the RA electrode and the return electrode. This path may be problematic for patient comfort reasons because pectoral tissue lies within the vector. A second current vector CV2, defined between the RA coil and the coronary sinus electrode would be an attractive vector were it not for the difficulty in placing and maintaining the electrode in the desired position.

Further referring to FIG. 1, the use of the RV electrode 22 as the return electrode serves to define a more attractive current vector than those described above. This is because a large portion of the current flows through the heart, along current vector component CV3. However, due to the low position of the RV coil, a substantial portion of the current exits the heart as shown with current vector component CV4. This often causes shock pain to the patient. Moreover, the low (actually referred to as the "apex") position of the conventional RV electrode during atrial cardioversion typically wastes energy by unnecessarily depolarizing the ventricles during delivery of the pulse between the RV electrode 22 and the RA electrode 20.

For ventricular defibrillation, a conventional shock vector SV1 is shown in FIG. 2, generally emanating from the single RV electrode 22 to the housing of the cardiac stimulation device 26 along a path of least resistance. Typically, the device generates a very large shock on the order of around four-hundred to eight-hundred volts between the electrode and the housing in an effort to stimulate enough of the heart tissue sufficient to terminate the fibrillation. Unfortunately, the conventional shock vector components tend to bypass the opposite ends of the septal wall, at 30 and 32 (in phantom), separating the right ventricle from the left ventricle. In some cases, enough cardiac tissue in these areas remains polarized to maintain the fibrillation activity, possibly necessitating prolonged shock therapy. Moreover, the shock magnitude often causes lingering pain for the patient after the restoration of consciousness.

A proposal that allegedly minimizes cardiac stimulation pain is described in U.S. Pat. No. 6,205,357 to Idecker et al. This proposal employs a plurality of electrodes, with at least one of the electrodes being disposed on the surface of the left ventricle. The pulse therapy utilizes a sequencing technique for delivering pulses with the left ventricular electrode. While this technique appears beneficial for its intended applications, it has drawbacks. For instance, in many circumstances the placement of the left ventricular electrode is very difficult. Moreover, maintaining the electrode in a stable position is also challenging.

In an effort to avoid the use of a left ventricular electrode for ventricular resynchronization, researchers have described a way of stimulating the left ventricle with a pair of right ventricular electrodes. The electrodes are placed such that a first electrode sits in the high basal region of the right ventricle, and a second electrode resides at the apex. Although the electrodes lie at different heights in the left ventricle, both are disposed proximate the septum at opposite ends. In employing this bifocal electrode arrangement, and applying specific pulses at appropriate timings, resynchronization of the ventricles may be accomplished in a manner similar to other resynchronization techniques that employ a left ventricular electrode.

What is needed and currently unavailable is a cardiac stimulation system and associated methods that deliver pulse therapies for both atrial and ventricular arrhythmias with minimal pain, and maximum efficiency. The system and methods described herein satisfy these needs.

SUMMARY

The bifocal cardiac stimulation system described herein provides a straightforward way of delivering atrial and ventricular pulse therapies with minimum patient pain, yet with maximum efficiency. Moreover, the system and methods support the generation of both monophasic and biphasic waveforms for maximum flexibility in therapy programming.

To realize the foregoing advantages, in one embodiment a cardiac stimulation system is provided. The cardiac stimulation system comprises first and second electrodes configured for positioning in a bifocal arrangement. A first lead system is adapted for carrying the first and second electrodes in the right ventricle in accordance with the bifocal arrangement and along the high basal region of the heart proximate the septum. A third electrode is adapted for positioning outside the right ventricle. The system further comprises a power supply and a controller. The controller is coupled to the power supply and operates to activate the first, second and third electrodes to deliver pulse therapy to the heart according to predetermined criteria.

In another embodiment, a method of stimulating a patient's heart by an implantable cardiac stimulation system is provided. The implantable cardiac stimulation system has a pair of spaced-apart electrodes disposed in the high basal region of the right ventricle on opposite sides of the septum, the method comprises the steps: detecting an arrhythmia; selecting an appropriate pulse therapy; and terminating the arrhythmia by delivering a first electrical pulse from between at least one of the pair of spaced-apart electrodes and a third electrode.

Other features and advantages will be apparent from the following detailed description when read in conjunction with the accompanying drawings.

BRIEF DESCRIPTION OF THE DRAWINGS

The various features of the bifocal cardiac stimulation system and the manner of attaining them will be described in greater detail with reference to the following description, claims, and drawings, wherein reference numerals are reused, where appropriate, to indicate a correspondence between the referenced items, and wherein:

FIG. 6 is a flowchart illustrating method steps for stimulating a patient's heart;

DETAILED DESCRIPTION

The following description is of the best mode presently contemplated. This description is not to be taken in a limiting sense but is made merely for the purpose of describing the general principles of the bifocal stimulation system and method. The scope of the invention should be ascertained with reference to the issued claims. In the description that follows, like numerals or reference designators will be used to refer to like parts or elements throughout.

As described above, a unique bifocal cardiac stimulation device is provided for minimizing patient pain and maximizing therapy efficiency.

The techniques described below are intended to be implemented in connection with any stimulation device that is configured or configurable to stimulate nerves and/or stimulate and/or shock a patient's heart.

Figure 1:
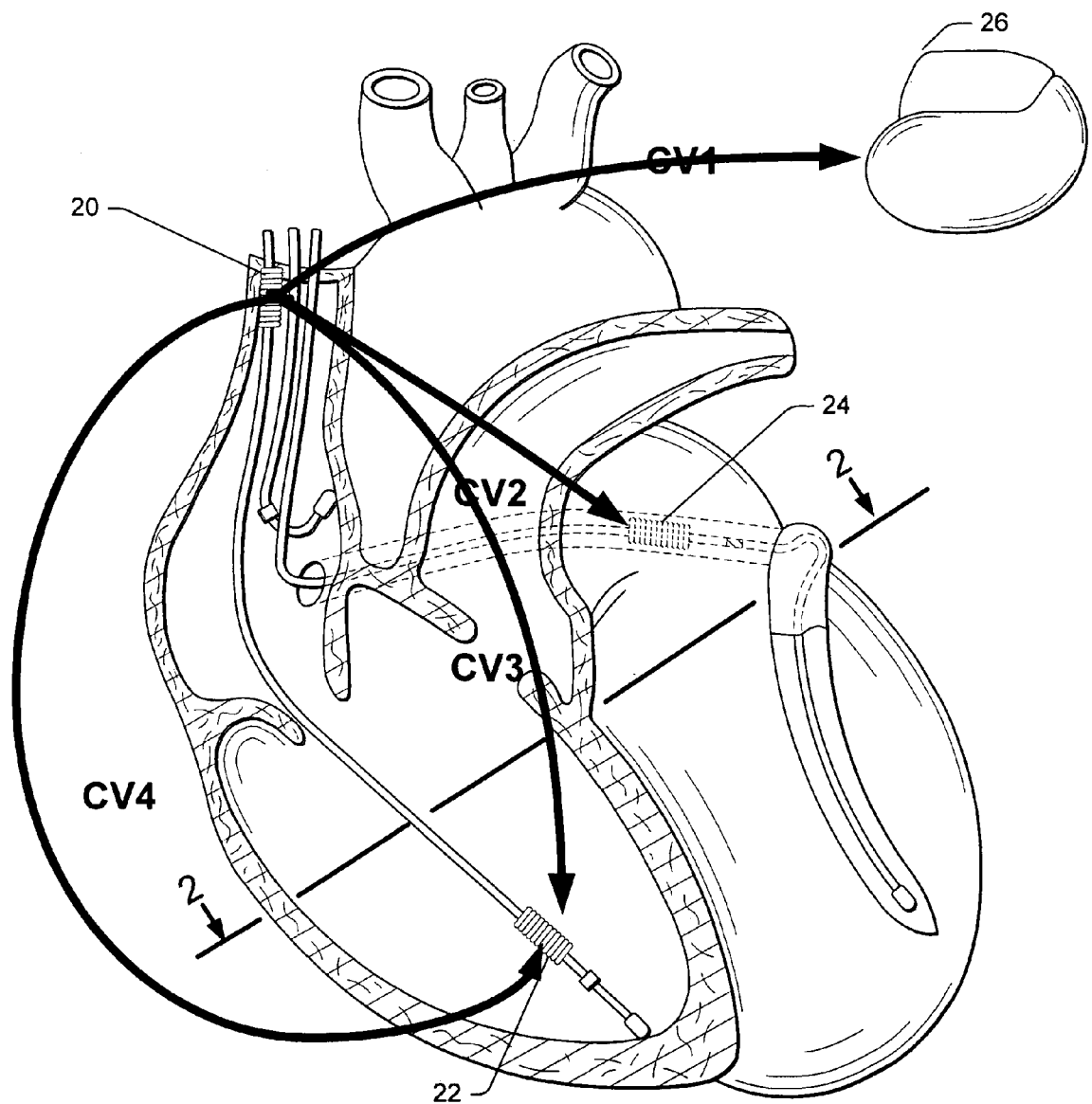
FIG. 1 is a simplified partial sectional view of a heart undergoing conventional atrial pulse therapy.
Figure 2:
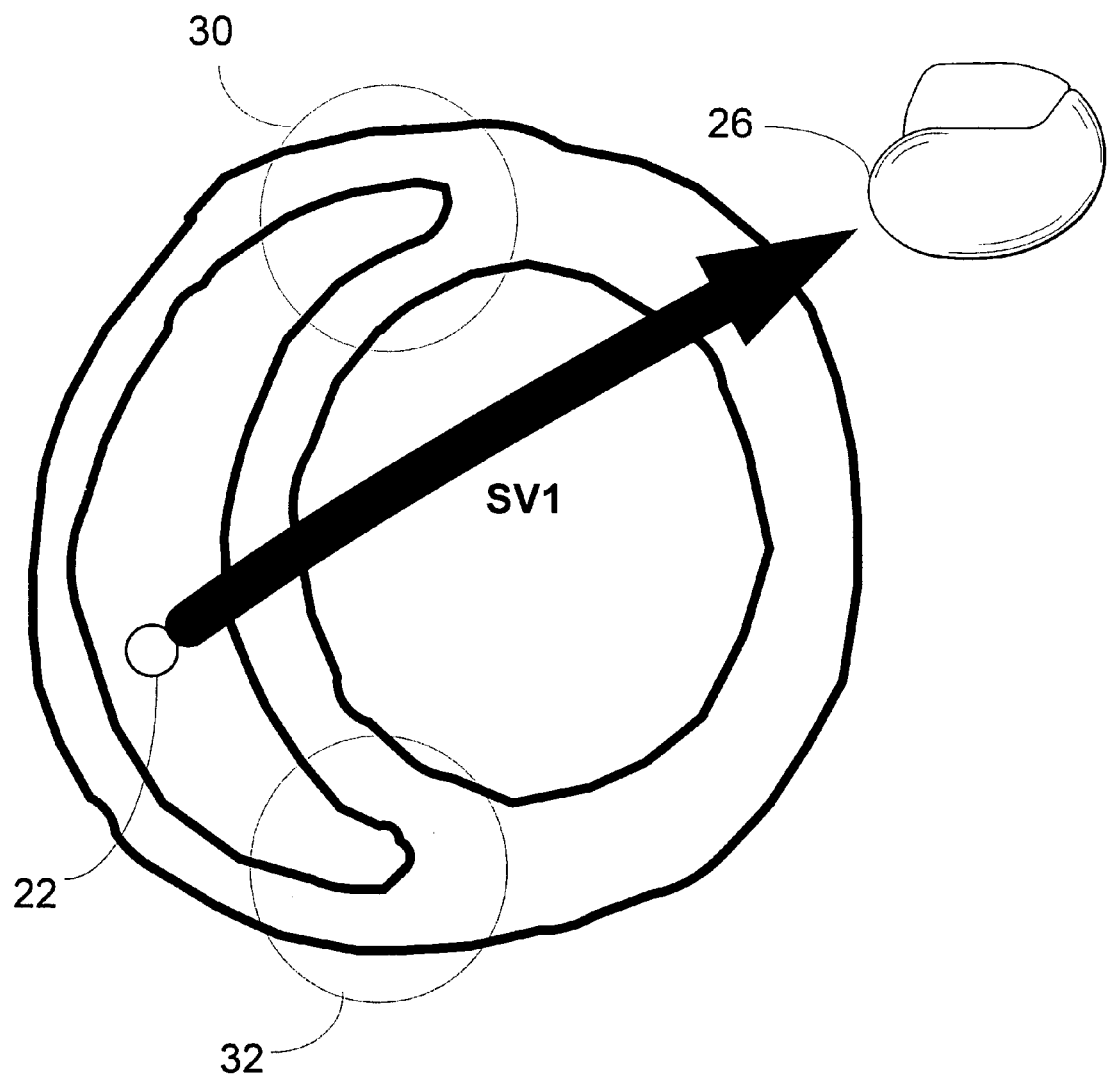
FIG. 2 is a partial transverse sectional view along line 2-2 of FIG. 1, illustrating a heart undergoing conventional ventricular pulse therapy.
Figure 3:
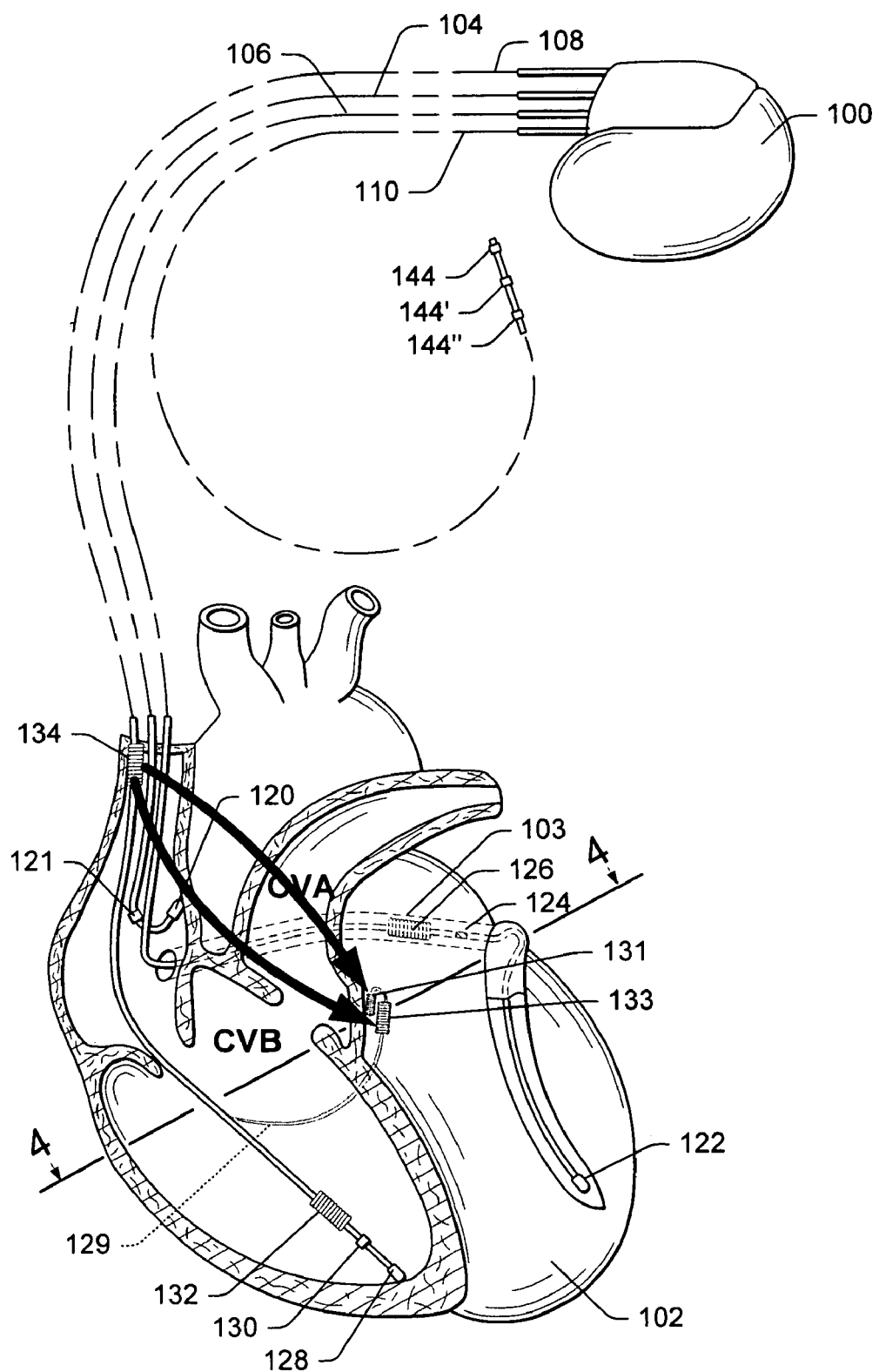
FIG. 3 is a simplified diagram illustrating an implantable cardiac stimulation device in electrical communication with a pair of bifocal RV electrodes implanted into a patients heart for delivering multi-chamber stimulation and shock therapy.

FIG. 3 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 3, the stimulation device 100 is coupled to an implantable right atrial lead 104 having, for example, an atrial tip electrode 120, which typically is implanted in the patient's right atrial appendage. The lead 104, as shown in FIG. 3, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in one implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

With continued reference to FIG. 3, in one particularly advantageous embodiment, the right ventricular lead 108 is adapted to form a lead system 129 (in phantom) that is inserted into the heart 102 to place a pair of coil electrodes 131 and 133 (in phantom) at spaced-apart anterior and posterior locations in the high basal region of the right ventricle, proximate the septal wall. Depending on the application, the electrodes may be unipolar or bipolar, as is well-known in the art. Further, the lead system may comprise a single pre-formed lead or a pair of leads, and is preferably constructed in accordance with well-known conductive gel techniques.

Figure 4:
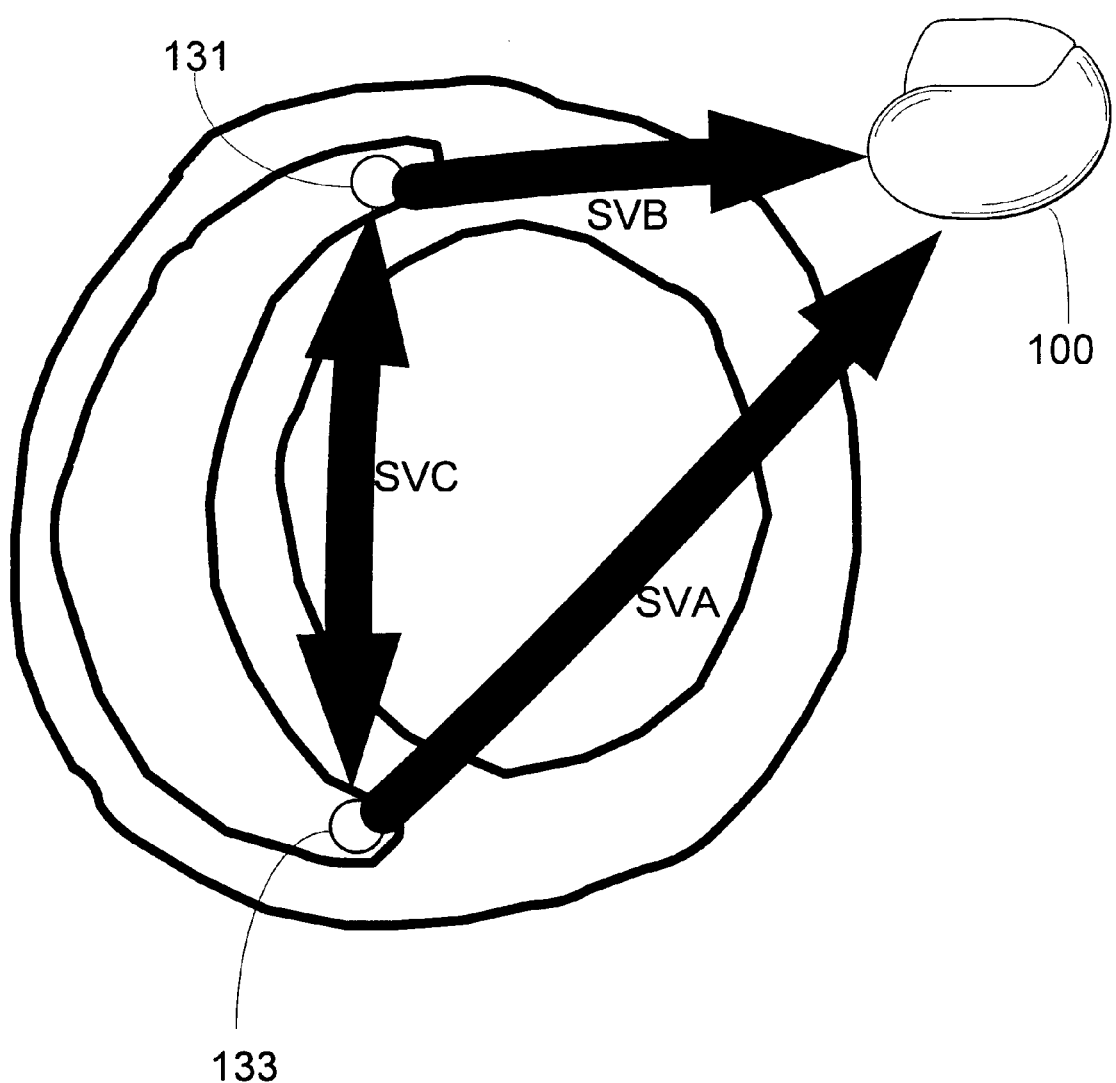
FIG. 4 is a partial transverse sectional view along line 4-4 of FIG. 3.

FIG. 4 illustrates the positioning of the bifocal electrodes 131 and 133 in further detail. This electrode placement takes advantage of the hearts own construction, where the right ventricle forms a bellows-type structure around a large portion of the left ventricle. The bifocal electrode placement in this manner allows for unique atrial and ventricular pulse therapies that minimize patient pain and maximize system efficiency as more fully described herein.

Figure 5:
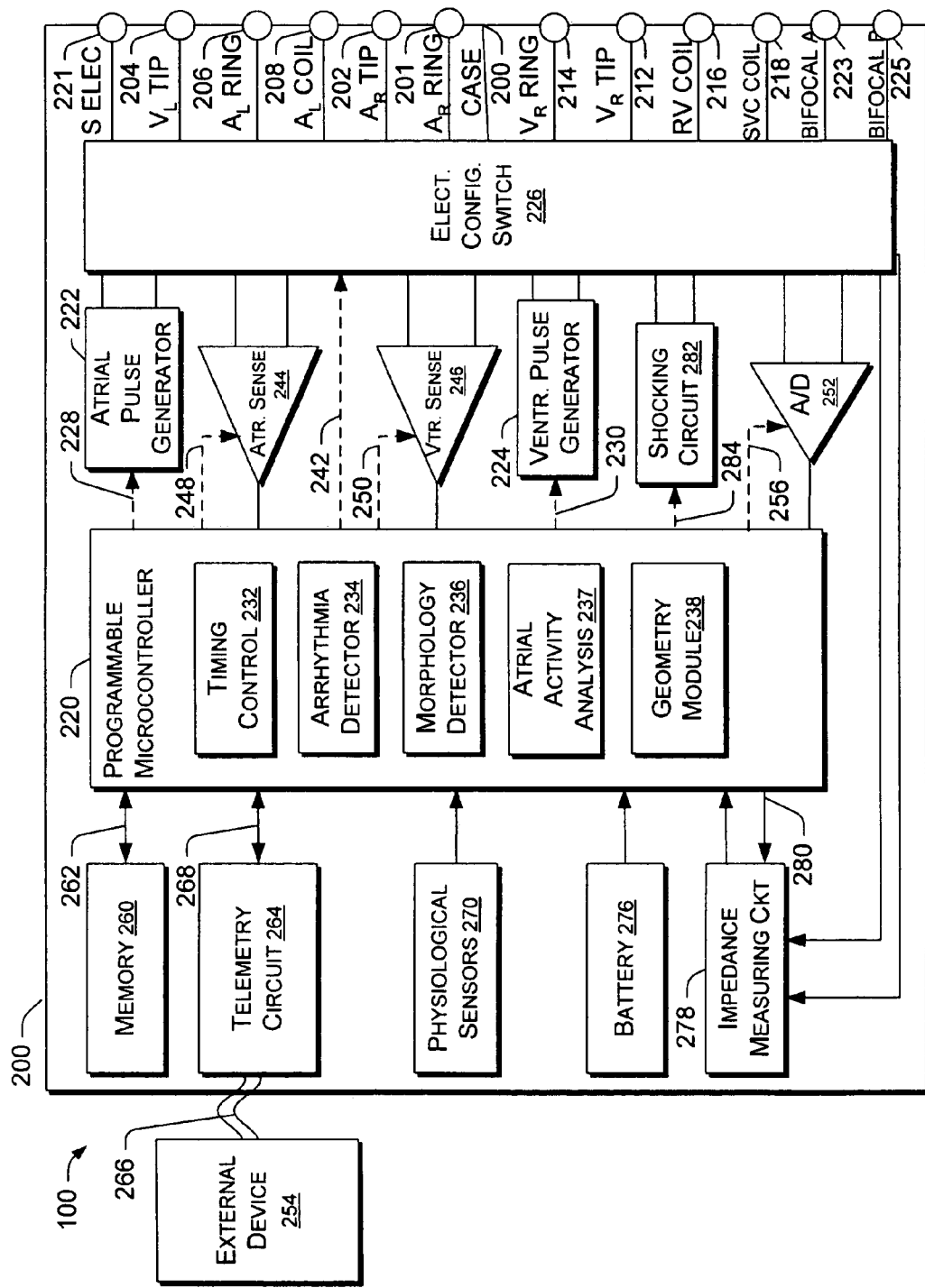
FIG. 5 is a functional block diagram of a multi-chamber implantable stimulation device illustrating the basic elements of a stimulation device that can provide cardioversion, defibrillation and pacing stimulation in four chambers of the heart.

FIG. 5 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 131, 132, 133 and 134 for shocking purposes. Housing 200 further includes a connector (not shown) having a plurality of terminals 201, 202, 204, 206, 208, 212, 214, 216, 218, 221, 223 and 225 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Respective bifocal electrode terminals BIFOCAL A and BIFOCAL B are adapted for connection to the bifocal RV electrodes 131 and 133. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 5 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 3. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an autonomic nerve stimulation module 238 for performing a variety of tasks related to autonomic nerve stimulation. This component can be utilized by the stimulation device 100 for determining desirable times to administer various therapies, including, but not limited to, parasympathetic stimulation. The autonomic module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled, for example, to the right atrial lead 104, the coronary sinus lead 106, and/or the right ventricular lead 108 through the switch 226 to sample signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 5. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrodes 131, 132, 133 and/or the SVC coil electrode 134.

As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Moreover, as more fully described below, advantageous therapies are made available when using the bifocal RV electrodes 131 and 133 in combination with the RA coil electrode 134 and/or the housing 200.

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As indicated above, a plurality of advantageous pulse therapy methods are available with the unique placement of the bifocal RV electrodes 131 and 133, illustrated in FIGS. 3 and 4. In FIG. 6, a flow chart is shown describing a pulse therapy method that takes advantage of the bifocal RV electrodes 131 and 133 to minimize patient pain, while maximizing pulse delivery efficiency. Generally, the method comprises first detecting an arrhythmia, at step 602, and selecting an appropriate pulse therapy, at step 604, to address the arrhythmia. Next, a first pulse is delivered, at step 606, from between at least one of the bifocal electrodes and another electrode, across the cardiac tissue of interest.

With continued reference to FIG. 6, following the delivery of the first pulse, at step 606, a determination is then made, at step 608, to see if the first pulse terminated the arrhythmia. If so, the therapy ends, at step 610. If not, a follow-on pulse is delivered, at step 606, followed by a subsequent determination step. This sequence of steps is iterated a predetermined number of cycles until either the arrhythmia stops, or a different therapy is initiated.

For atrial cardioversion applications, the general method described above using the bifocal RV electrodes 131 and 133 with the RA electrode 134 may be implemented a variety of ways to achieve different benefits for different circumstances. For atrial cardioversion applications, the bifocal RV electrodes allow for substantially pain free current vectors CVA and CVB, between the right atrial coil electrode 134 and the bifocal electrodes. This is illustrated more clearly in FIG. 3.

Atrial cardioversion pulse therapies typically involve pulses in the range of one-hundred to four-hundred volts. For instance, as one example, a first monophasic or biphasic pulse may be delivered between the RA electrode 134 and the posterior RV electrode 131, followed immediately thereafter by a second pulse from between the RA electrode and the anterior RV electrode 133.

Biphasic waveforms are often used to provide energy efficient stimulation for enhancing battery life. In contrast with monophasic waveforms that generally deliver current to the patient in a single polarity, biphasic waveforms reverse the direction of current flow part-way through the pulse. Biphasic waveforms thus contain both positive and negative components.

Figure 7A:
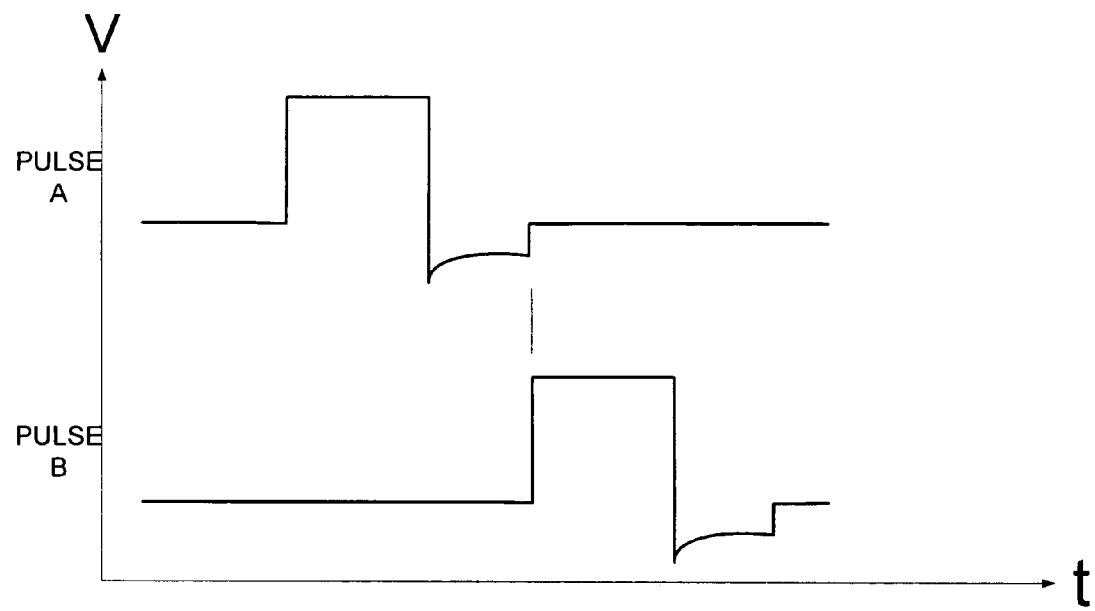
FIGS. 7A, 7B and 8 comprise graphs illustrating biphasic waveforms delivered in accordance with the method of FIG. 6.
Figure 7B:
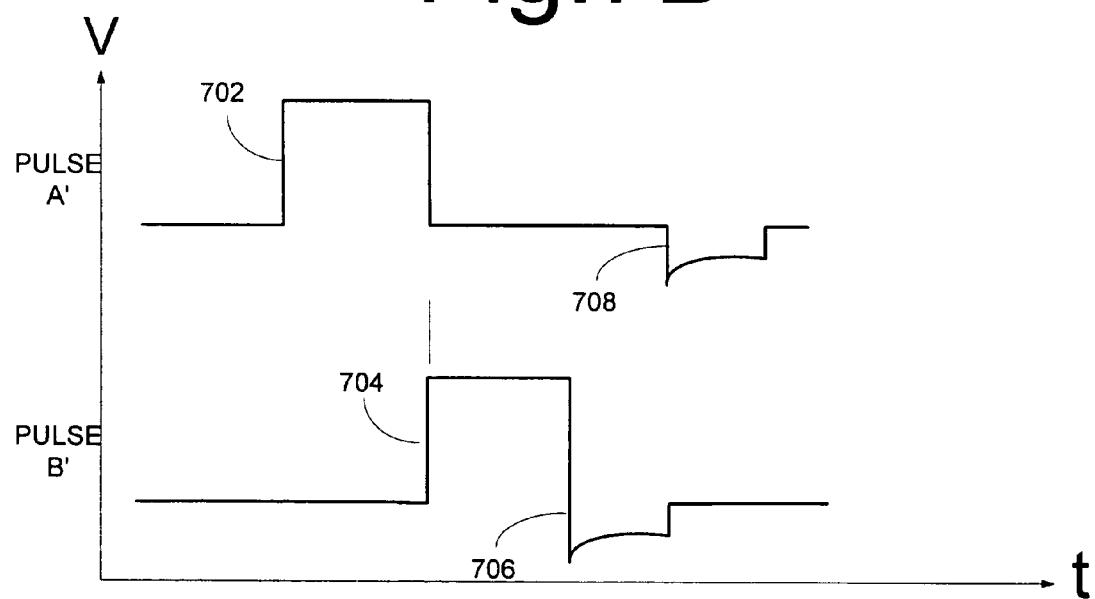

FIGS. 7A and 7B illustrate biphasic waveform sequencing schemes that take advantage of the method described above. In FIG. 7A, each pulse (PULSE A, PULSE B) delivered between the RA electrode 120 and one of the RV electrodes 131 or 133 comprises a full biphasic waveform in sequence. In other words, the second waveform is delayed until completion of the entire first waveform.

In the alternative sequencing scheme of FIG. 7B, efficiency may be maximized for delivering pulses PULSE A' and PULSE B' by delaying the negative portions of the biphasic waveforms, at 706 and 708, until the positive phases, at 702 and 704, have been delivered to both electrodes. This scheme allows the same capacitors to deliver the pulses to both electrodes before having to recharge.

One of the key benefits to delivering pulses sequentially in the manner described above is the reduction in energy applied to the cardiac tissue for each pulse. Minimizing pulse energy correspondingly reduces patient discomfort in the event any current conduction occurs outside the heart. Energy is also efficiently managed due to the high basal placement of the RV electrodes. This minimizes any wasted energy that might otherwise be used to unnecessarily depolarize the ventricles during atrial cardioversion Although sequential pulsing for atrial cardioversion works well with the bifocal RV electrodes 131 and 133 to minimize patient pain, the desirable placement of the electrodes allows for simultaneous pulses between each of the electrodes and the RA electrode 134 as well. This may be desirable in lieu of sequential pulsing for some circumstances.

In ventricular fibrillation applications, the general pulse method described above for use with the bifocal RV electrodes 131 and 133 is especially advantageous. As shown in FIG. 4, the positioning of the RV electrodes at the anterior and posterior ends of the right ventricle enables the electrodes to establish a shock vector SVC across the septal wall separating the right ventricle from the left ventricle. Additionally, each electrode may establish relative shock vectors SVA and SVB between the relative electrode locations and the housing of the cardiac stimulation device 100. With this array of shock vectors available, the general method described above may be optimized for maximum patient benefit.

As an alternative to using the housing 200 as a return electrode, the left ventricular electrode 126 (FIG. 3) may be employed in the ventricular defibrillation method described above. Use of this electrode further minimizes the amount of non-cardiac tissue disposed in the shock vectors, thereby minimizing patient discomfort.

Figure 8:
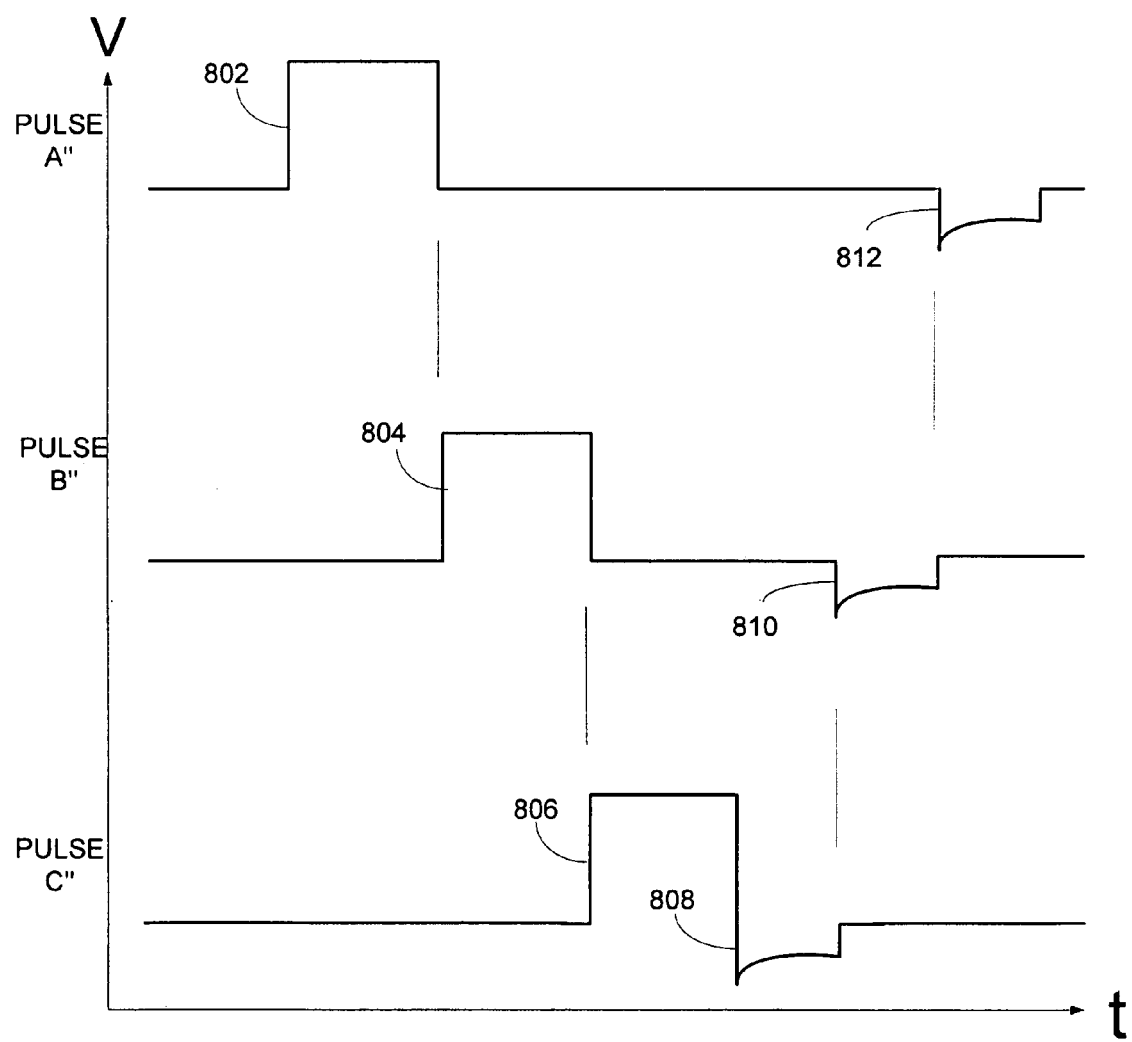

As one example of a ventricular defibrillation technique, all three of the shock vectors SVA, SVB and SVC (FIG. 4) described above may be established through a sequenced pulsing scheme similar to that described above in the context of atrial cardioversion, and illustrated graphically in FIG. 8. For purposes of clarity, the pulse durations and magnitudes are not shown to scale. In this example, the anterior wall is first shocked with a pulse, at 802, of a first duration (for example, 3 ms), followed by the posterior portion of the left ventricle with a similar pulse, at 804, (for example 4 ms to account for the reduction in capacitive charge), and concluding with the septal wall with a third pulse, at 806, (of, for example, 5 ms). Similar to the atrial cardioversion technique detailed above, efficiency may be maximized by delaying all of the negative portions of the waveforms at 808, 810 and 812. Determinations may be made after each pulse to determine whether the fibrillation has terminated.

As an alternative technique to the sequencing scheme described above, a first shock may be delivered between the bifocal electrodes 131 and 133 to stimulate the septal wall, followed by a main shock to the housing from both bifocal electrodes simultaneously. This technique allows each of the shocks to be of somewhat higher energy than the multiple-pulse sequencing technique described above.

Because of the typical high-energy nature of ventricular defibrillation shocks, having the capability and flexibility to defibrillate with a variety of energy pulse levels is important for minimizing patient discomfort when consciousness is regained.

Another advantage in employing the bifocal RV electrodes 131 and 133 for ventricular defibrillation involves the thoroughness of the shock vector coverage. Depolarizing as much cardiac tissue as possible with the defibrillation shocks is important to successfully terminate the fibrillation as quickly as possible. Moreover, depolarizing the septum may be done directly by the bifocal RV electrodes to facilitate enhanced defibrillation.

Use of the bifocal RV electrodes 131 and 133 disclosed herein is also beneficial in the context of anti-tachycardia pacing, or ATP. This form of therapy is often characterized by low-voltage pacing pulses, on the order of around one to ten volts. For ATP applications, the vector defined across the septal wall due to the placement of the bifocal RV electrodes tends to depolarize much more of the ventricular mass than a classical single-tip and ring scheme in the right ventricular apex. With the bifocal electrodes comprising tip electrodes in this application, the current passes directly between the tip positioned at the anterior location, and the tip in the posterior position.

Alternatively, for ATP applications, both of the RV electrodes comprise bipolar (tip/ring) pairs (not shown) capable of generating their own ATP waveforms. In one embodiment, high pacing levels of current between the coils of the RV electrodes generate large rapidly propagating fields that tend to overcome any waveforms emanating from a ventricular tachycardia focus. This leads to significantly better ATP performance.

Patients undergoing congestive heart failure (CHF) therapy with an implantable cardiac stimulation device can also receive advantages due to the implementation of the bifocal RV electrodes 131 and 133 described above. For example, passing current between the electrodes leads to very crisp contractions for CHF therapy. This is also useful in the initial states of orthostatic hypotension because of the contraction generation benefits. Further, because the electrodes remain near the heart, the risk of painful larger currents to a sub-pectoral housing is largely eliminated.

Those skilled in the art will recognize the many benefits and advantages afforded by the bifocal cardiac stimulation system disclosed herein. Of significant importance is the implementation of a pair of right ventricular electrodes in an advantageous bifocal relationship useful for a variety of applications. The pulse therapies made possible by the use of the bifocal electrodes establishes current vectors that minimize patient pain and maximize system efficiency.

While the bifocal stimulation system has been particularly shown and described with reference to the preferred embodiments thereof, it will be understood by those skilled in the art that various changes in form and detail may be made therein without departing from the spirit and scope of the invention.

What is claimed is:

1. A cardiac stimulation system for implantation in a patient, the cardiac stimulation system comprising:
    first and second electrodes configured for positioning in a bifocal arrangement within a right ventricle;
    a first lead system adapted for carrying the first and second electrodes in the high basal region of the right ventricle at generally opposite sides of the right ventricle;
    a third electrode adapted for positioning outside the right ventricle;
    a power supply; and
    a controller coupled to the power supply and operative to activate the first, second and third electrodes to deliver pulse therapy to the heart according to predetermined criteria.

2. A cardiac stimulation system according to claim 1 wherein:
    the first electrode is adapted for disposition in the posterior high basal region of the right ventricle proximate the septum, and the second electrode is adapted for disposition in the anterior high basal region of the right ventricle proximate the septum.

3. A cardiac stimulation system according to claim 1 wherein:
    the power supply and the controller are housed in a metallic housing, and the third electrode comprises the metallic housing.

4. A cardiac stimulation system according to claim 1 wherein:
    the third electrode is adapted to be disposed in the right atrium.

5. A cardiac stimulation system according to claim 1 wherein:
    the third electrode is adapted to be disposed in the left ventricle.

6. A cardiac stimulation system according to claim 1 wherein:
    the first lead system comprises a single pre-formed lead.

7. A cardiac stimulation system according to claim 1 wherein:
    the first lead system comprises a pair of leads, each lead adapted for carrying one of the first and second electrodes.

8. A cardiac stimulation system according to claim 1 wherein at least one of the first and second electrodes comprises an electrode from the group comprising a tip electrode, a bipolar electrode, and a coil electrode.

9. A cardiac stimulation system for implantation in a patient to stimulate the patient's heart, the cardiac stimulation system comprising:
    first and second electrodes configured for positioning in a bifocal arrangement;
    a first lead system adapted for carrying the first and second electrodes in the right ventricle in accordance with the bifocal arrangement along the high basal region of the heart proximate the septum and on generally opposite sides of the right ventricle;
    a third electrode adapted for positioning outside the right ventricle;
    a power supply; and
    a controller coupled to the power supply and operative to activate the first, second and third electrodes to deliver pulse therapy to the heart according to predetermined criteria.

10. A method of defibrillating a patient's heart by an implantable cardiac stimulation system, the implantable cardiac stimulation system having a controller encased in a metallic housing and a pair of spaced apart electrodes disposed in the high basal region of the right ventricle on generally opposite sides of the right ventricle, the method comprising:
    detecting ventricular fibrillation; and
    delivering at least one first electrical pulse between the pair of electrodes within the right ventricle.

11. A method of defibrillating a patient's heart according to claim 10 and further comprising:
    determining the effectiveness of the at least one electrical pulse in terminating the ventricular fibrillation; and
    delivering a second electrical pulse from between at least one of electrode the pair of electrodes and the metallic housing if the first pulse is ineffective.

12. A method of defibrillating a patient's heart according to claim 11 and further comprising:
    determining the effectiveness of the second electrical pulse in terminating the ventricular fibrillation; and
    delivering a third electrical pulse from between at least one electrode of the pair of electrodes and the metallic housing if the second pulse is ineffective.

13. A method according to claim 11 wherein the cardiac stimulation system further comprises a left ventricular electrode, and wherein delivering a second electrical pulse comprises:
    delivering a second electrical pulse between at least one electrode of the pair of electrodes and the left ventricular electrode.

14. A method according to claim 10 wherein:
    the first electrical pulse comprises a biphasic waveform having respective first positive and first negative components.

15. A method of stimulating a patient's heart by an implantable cardiac stimulation system, the implantable cardiac stimulation system having a controller encased in a metallic housing and a pair of spaced-apart electrodes disposed in the high basal region of the right ventricle on opposite sides of the ventricle, the method comprising:
    detecting an arrhythmia;
    selecting an appropriate pulse therapy; and delivering at least one electrical pulse between the pair of spaced-apart electrodes.

16. A method according to claim 15 wherein the implantable cardiac stimulation system has a third electrode positioned outside the right ventricle, and further comprising:
   determining the effectiveness of the first electrical pulse in terminating the arrhythmia; and
   delivering a second electrical pulse from between at least on electrode of the pair of electrodes and the third electrode if the first pulse is ineffective.

17. A method according to claim 15 wherein selecting an appropriate pulse therapy comprises:
   selecting an anti-tachycardia pacing therapy for generating electrical pulses in the range of 0 to 10 volts.

18. A method according to claim 15 wherein selecting an appropriate therapy comprises:
   selecting an atrial cardioversion pulse therapy for generating electrical pulses in the range of 10 to 400 volts.

19. A method according to claim 15 wherein selecting an appropriate therapy comprises:
   selecting a ventricular defibrillation pulse therapy for generating electrical pulses in the range of 400 to 800 volts.

20. A method according to claim 15 wherein selecting an appropriate therapy comprises:
   selecting a heart failure pulse therapy.

21. A method of cardioverting the atria by an implantable system, the implantable system having a controller and a pair of right ventricular electrodes disposed in a bifocal arrangement in the high basal region of the right ventricle proximate the septum and at opposing anterior and posterior sides, the implantable system further comprising a third electrode disposed in the right atrium, the method comprising the steps:
   detecting an atrial arrhythmia; and
   delivering a first electrical pulse between the third electrode and at least one of the right ventricular electrodes.

22. A method according to claim 21 and further comprising:
   determining the effectiveness of the first electrical pulse in terminating the atrial arrhythmia; and
   delivering a second electrical pulse between the third electrode and the other electrode of the pair of electrodes if the first pulse is ineffective.

* * * * *